US008124374B2

(12) United States Patent
Shoji et al.

(10) Patent No.: US 8,124,374 B2
(45) Date of Patent: *Feb. 28, 2012

(54) METHOD OF PRODUCING RECOMBINANT PROTEIN

(75) Inventors: Hiroshi Shoji, Moriya (JP); Toshikazu Sugimoto, Moriya (JP)

(73) Assignee: Asahi Breweries, Ltd., Tokyo (JP)

(*) Notice: Subject to any disclaimer, the term of this patent is extended or adjusted under 35 U.S.C. 154(b) by 142 days.

This patent is subject to a terminal disclaimer.

(21) Appl. No.: 12/090,022

(22) PCT Filed: Sep. 26, 2006

(86) PCT No.: PCT/JP2006/319028
§ 371 (c)(1),
(2), (4) Date: Apr. 11, 2008

(87) PCT Pub. No.: WO2007/043330
PCT Pub. Date: Apr. 19, 2007

(65) Prior Publication Data
US 2009/0233332 A1    Sep. 17, 2009

(30) Foreign Application Priority Data

Oct. 12, 2005  (JP) ................................. 2005-297732
Mar. 23, 2006  (JP) ................................. 2006-080477

(51) Int. Cl.
*C12P 21/06* (2006.01)
*C12P 21/04* (2006.01)
*C12N 15/74* (2006.01)

(52) U.S. Cl. ........................ 435/69.1; 435/70.1; 435/471
(58) Field of Classification Search .......................... None
See application file for complete search history.

(56) References Cited

U.S. PATENT DOCUMENTS

| 4,358,462 | A  | 11/1982 | Takeda |
| 6,667,066 | B2 | 12/2003 | Labeille et al. |
| 6,843,994 | B2 | 1/2005  | Iwasaki |
| 2004/0082053 | A1 | 4/2004 | Machida et al. |
| 2007/0207238 | A1 | 9/2007 | Sugimoto et al. |

FOREIGN PATENT DOCUMENTS

| EP | 1734109 A1 | 12/2006 |
| EP | 1908818 A1 | 4/2008 |
| JP | 59-140872 A | 8/1984 |
| JP | 61-293380 A | 12/1986 |
| JP | 3-247265 A | 11/1991 |
| JP | 7-177884 A | 7/1995 |
| JP | 8-23955 A | 1/1996 |
| JP | 10-204494 A | 8/1998 |
| JP | 11-225746 A | 8/1999 |
| JP | 2001-321154 A | 11/2001 |
| JP | 2003-047455 | 2/2003 |
| JP | 2003-47455 A | 2/2003 |
| JP | 2003-250588 | 9/2003 |
| JP | 2003-250588 A | 9/2003 |
| JP | 2003-265165 | 9/2003 |
| JP | 2004-267065 A | 9/2004 |
| JP | 2004242532 A | 9/2004 |
| JP | 2004-290155 A | 10/2004 |
| JP | 2005295871 A | 10/2005 |
| JP | 2005295873 A | 10/2005 |
| JP | 2005318886 A | 11/2005 |
| WO | 96/11264 A1 | 4/1996 |
| WO | 2004072280 A1 | 8/2004 |
| WO | 2005/097967 A1 | 10/2005 |
| WO | 2007/010979 A1 | 1/2007 |
| WO | 2007/039990 A1 | 4/2007 |

OTHER PUBLICATIONS

Nomachi et al., Molecular Breeding of *Aspergillus kawachii* Over-producing Cellulase and Its Application to Brewing Barley Shochu., Journal of Bioscience and Bioengineering, 2002, vol. 93, pp. 382-387.*

Definition of husk (last viewed on Apr. 8, 2010).*

Murakami, Classification of the Koji Mold, J. Gen. Appl. Microbiol., 1971, vol. 17, pp. 281-309.*

Bhargava et al., Pulsed Addition of Limiting-Carbon During *Aspergillus oryzae* Fermentation Leads to Improved Productivity of Recombinant Enzyme; Biotechnol Bioeng, 2003, vol. 82, pp. 111-117.*

Kinoshita et al., Cloning of the xynNB Gene Encoding Xylanse B from *Aspergillus niger* and Its Expression in *Aspergillus kawachii*; Journal of Fermentation and Bioengineering, 1995, vol. 79, pp. 422-428.*

Gomi et al., Transformation of the industrial strain of *Aspergillus oryzae* with the homologous amdS gene as a dominant selectable marker; Journal of Fermentation and Bioengineering, 1992, vol. 74, pp. 389-391.*

Kozo Tsuchiya, et al, "High Level Secretion of Calf Chymosin Using a Glucoamylase-Prochymosin Fusion Gene in *Aspergillus oryzae*", Biosci, Biotech, Biochem, 1994, pp. 895-899, vol. 58, No. 5.

Kozo Tsuchiya, et al., "High Level Secretion of Calf Chymosin Using a Glucoamylase-prochymosin Fusion Gene in *Aspergillus oryzae*", Biosci. Biotech. Biochem., 1994, 58(5):895-899.

Yoji Hata et al., "Glucoamylase-Encoding Genes of *Aspergilllus oryzae*", Journal of the Society for Biotechnology, Japan, 2000, 78(4): 120-127.

Akitsugu Kawato et al., "High Production Mechanism of Glucoamylases in Solid Malt", Journal of Fushimi Joyu-kai, 1998, 13:15-25.

Kiyoshi Ito, Progress of *Aspergillus* Mold Study: Molecular Genetic Analysis of Shochu Koji Molds, J. Brew. Soc., Japan, 2000, 95(9):635-640.

(Continued)

Primary Examiner — Alexander Kim
(74) Attorney, Agent, or Firm — Sughrue Mion, PLLC

(57) ABSTRACT

An object of the present invention is to provide a method of mass-producing recombinant protein by the liquid culture method with koji molds as host. According to the present invention, it is provided a method of producing recombinant protein by using the recombinant koji molds which are obtained by transforming koji molds as host comprising: culturing the recombinant koji molds in a liquid medium which contains as culture raw material at least one selected from the group consisting of the cereal of which surface is entirely or partly covered with at least husks, the bean and/or the tuber of which surface is covered with hulls and the amaranthus and/or the quinoa without pre-treatment such as grinding or crushing; and collecting the recombinant protein from the culture product.

8 Claims, No Drawings

OTHER PUBLICATIONS

Taku Kato et al., "Analysis of the unique expression mode of acid-unstable α-amylase from *Aspergillus kawachii*", J. Brew. Soc., Japan, 2005, 100(7):513-519.

Kimio Iwano et al., "Influence of the variety of rice and polishing rate on Japanese sake koji making", J. Brew. Soc., Japan, 2004, 99(1):55-63.

Takeshi Akao, et al. "Honkaku-shochu Production Using Shaking Cultured Medium of *Aspergillus kawachii*", J. Brew. Soc. Japan, 1994, 89(11): 913-914 (with English Translation).

Annual Report from Aichi Food Research Center, 2001, The 42nd Issue (with English Translation).

A. Blandino et al., "Utilization of whole wheat flour for the production of extracellular pectinases by some fungal strains", Process Biochemistry, 2001, 37(5): 497-503.

Hisashi Fukuda et al., "Improvement of Material Utilization in Sake Moromi Brewing by Addition of Cell Wall Macerating Enzymes", Seibutsu-kogaku, 2001, 79: 299-302 (with Partial English Translation).

Hisashi Fukuda, et al. "Improvement of Material Utilization in Sake Moromi Brewing by Addition of Cell Wall Macerating Enzymes", J. Brew. Soc. Japan, 2002, 97(12): 808-813 (with English Translation).

D.V. Gokhale, et al., "Optimization of Cellulase Production by *Aspergillus niger* NCIM 1207", Appl. Biochem. Biotechnol., 1991, 30(1): 99-109.

Masatoshi Goto, "Digestion of raw starch by glucoamylase I from *Aspergillus awamori* var. *kawachi*", Bioscience & Industry, 2001, 59(3): 183-184 (with English Translation).

Walter P. Hammes et al., "Microbial ecology of cereal fermentations", Trends in Food Science & Technology, 2005, 16: 4-11.

Kimio Iwano, et al., "Influence of Cultural Conditions on Various Enzyme Activities of Shochu Koji", Journal of the Brewing Society of Japan, 1987, 82(3): 200-204 (with Partial English Translation).

Keiji Kainuma, "Special-Brewing and Synthesis—Enzymes to Degrade Raw Starch", Kobunshi, 1986, 35(6): 564 (with English Translation).

Yojiro Koba et al., "Preparation of Koji from Corn Hulls for Alcoholic Fermentation without Cooking", J. Fement. Technol., 1986, 64(2): 175-178.

D.D. Mariani et al., "Influence of amaranth on the production of alpha-amylase using *Aspergillus neger* NRRL 3112", Rev. Argent Microbiol., 2000, 32(4): 185-189 (Abstract).

Susumu Masuda et al., "Analysis of Enzyme Production by Submerged Culture of *Aspergillus oryzae* Using Whole Barley", Bioscience, Biotechnology, and Biochemistry, 2009, 73(10): 2190-2195.

Rikke Morkeberg et al., "Induction and repression of α-amylase production in batch and continuous cultures of *Aspergillus oryzae*", Microbiology, 1995, 141(10): 2449-2454.

Hideki Narahara et al., "Study on Production of Rice Koji (The Second Report) Influence Factor on Enzyme Production of *Aspergillus oryzae*", Miso Science and Technology, 1983, 31(9): 358-363 (with English Translation).

C. Adinarayana Reddy et al., "Glucose feedback inhibition of amylase activity in *Aspergillus* sp. and relase of this inhibition when cocultured with *Saccharomyces cerevisiae*", Enzyme Microbe. Technol., 1986, 8: 659-664.

Masashi Sato et al., "The Effect of Polishing Rate of Rice on the Quality of Koji and Miso", Report of the Shinshu-Miso Research Institute, 1989, pp. 1-2 (with Partial English Translation).

Shigehisa Shibata et al., Knowledge of Flours; revised and enlarged edition, Saiwai Shobo K.K., 2000, pp. 72-73 (with English Translation).

Masahiko Shimoda et al., "Characteristics of Water Uptake of Australian Polished Barley in Shochu-Making", J. Inst. Brew., Jan.-Feb. 1998, 104: 33-35.

Hiroshi Shoji et al. "Analysis of the Factor That Affect the Productivity of the Enzyme Contained in the Submerged Culture of *Apergillus kawachii* Using Whole Barley", The Society for Biotechnology Taikai Koen Yoshishu, (Mar. 8, 2006), 58: 68 (with English Translation).

Hiroshi Shoji et al., "Simultaneous Production of Glucoamylase and Acid-Stable a-Amylase Using Novel Submerged Culture of *Aspergillus kawachii* NBRC4308", Journal of Bioscience and Bioengineering, 2007, 103(2): 203-205.

K.R. Sreekantiah et al., "Effekt of Cultural and Nutritional Variations on Certain Exo-Enzymes Secreted by Fungi", Chem. Mikrobiol. Technol. Lebensm, 1973, 2: 42-48.

Shigetoshi Sudo et al., "Comparison of Acid-Stable a-Amylase Production by *Apspergillus kawachii* in Solid-State and Submerged Cultures", Journal of Fermentation and Bioengineering, 1994, 77(5): 483-489.

Shigetoshi Sudo; "Characteristics of Acid-Stable Alpha Amylase Production by *Aspergillus kawachii*", Journal of the Brewing Society of Japan, 1994, 89: 768-774 (with English Translation).

Toshikazu Sugimoto et al., "Enzyme Production of *Aspergillus kawachii* in Submerged Cultivation Using Original Barley", The Society for Biotechnology Taikai Koen Yoshishu, (Mar. 8, 2006), 58: 69 (with English Translation).

Yuji Teramoto et al., "Thai ou: Characteristics of a traditional Thai alcoholic beverage drunk with a straw", the BREWER International, 2002, 2(7): 31-32.

Hiroharu Tokuda et al., "Hydrolysis of Raw Starch with Immobilized Mycelia", The Society for Biotechnology, Japan Taikai Koen Yoshisu, 1996: 69 (with English Translation).

Ryozo Tonoike, Dictionary of Liquour, Tokyodo Syuppan K.K., 1980, pp. 79-81 (with English Translation).

Poorna Viswanathan et al., "Production of a-amylase with *Aspergillus flavus* on Amaranthus grains by solid-state fermentation", J. Basic Microb. Technol., 2001, 41(1): 57-64.

Hitoshi Wadaka et al., "Preparation of Submerged Mold Culture Fluid for Rice Vinegar Mash", 1980, 15: 13-19 (Partial Translation).

Ruohang Wang et al., "Protease production and conidiation by *Aspergillus oryzae* in flour fermentation", Process Biochemistry, 2005, 40(1): 217-227.

Final Office Action issued Oct. 26, 2010, in U.S. Appl. No. 11/547,809 (in the name of Toshikazu Sugimoto).

Non-Final Office Action issued Mar. 15, 2011, in U.S. Appl. No. 11/995,942 (in the name of Toshikazu Sugimoto).

Final Office Action issued Jan. 4, 2011, in U.S. Appl. No. 12/067,423 (in the name of Toshikazu Sugimoto).

Non-Final Office Action issued Dec. 28, 2010, in U.S. Appl. No. 12/089,067 (in the name of Toshikazu Sugimoto).

* cited by examiner

```
                        SEQUENCE LISTING

<160> NUMBER OF SEQ ID NOS: 20

<210> SEQ ID NO 1
<211> LENGTH: 22
<212> TYPE: DNA
<213> ORGANISM: Aspergillus kawachii

<400> SEQUENCE: 1
ccagctcgac ctatagcagc at                                             22

<210> SEQ ID NO 2
<211> LENGTH: 20
<212> TYPE: DNA
<213> ORGANISM: Aspergillus kawachii

<400> SEQUENCE: 2
aagtctgatg gcgacgagct                                                20

<210> SEQ ID NO 3
<211> LENGTH: 17
<212> TYPE: DNA
<213> ORGANISM: Aspergillus kawachii

<400> SEQUENCE: 3
cggcacggca gatgatc                                                   17

<210> SEQ ID NO 4
<211> LENGTH: 23
<212> TYPE: DNA
<213> ORGANISM: Aspergillus kawachii

<400> SEQUENCE: 4
gaatgtacct catggtcgac gtc                                            23

<210> SEQ ID NO 5
<211> LENGTH: 19
<212> TYPE: DNA
<213> ORGANISM: Aspergillus kawachii

<400> SEQUENCE: 5
acactcctgg gcacattcg                                                 19

<210> SEQ ID NO 6
<211> LENGTH: 21
<212> TYPE: DNA
<213> ORGANISM: Aspergillus kawachii

<400> SEQUENCE: 6
ttacaccaac gacatagccc t                                              21

<210> SEQ ID NO 7
<211> LENGTH: 21
<212> TYPE: DNA
<213> ORGANISM: Aspergillus niger

<400> SEQUENCE: 7
actgaacaag ctcctgggtc a                                              21
```

<210> SEQ ID NO 8
<211> LENGTH: 19
<212> TYPE: DNA
<213> ORGANISM: Aspergillus niger

<400> SEQUENCE: 8
ccagggtggt gtcctcccc                                                19

<210> SEQ ID NO 9
<211> LENGTH: 21
<212> TYPE: DNA
<213> ORGANISM: Aspergillus awamorii

<400> SEQUENCE: 9
ttttgggact ggcctttagc t                                             21

<210> SEQ ID NO 10
<211> LENGTH: 21
<212> TYPE: DNA
<213> ORGANISM: Aspergillus awamorii

<400> SEQUENCE: 10
ttcttcgaca ccgtcaagtc c                                             21

<210> SEQ ID NO 11
<211> LENGTH: 20
<212> TYPE: DNA
<213> ORGANISM: Aspergillus oryzae

<400> SEQUENCE: 11
cgtgcagatc gtccaaacct                                               20

<210> SEQ ID NO 12
<211> LENGTH: 20
<212> TYPE: DNA
<213> ORGANISM: Aspergillus oryzae

<400> SEQUENCE: 12
acttctcacg gccaacaacc                                               20

<210> SEQ ID NO 13
<211> LENGTH: 19
<212> TYPE: DNA
<213> ORGANISM: Aspergillus oryzae

<400> SEQUENCE: 13
cactcctggg cacattcgt                                                19

<210> SEQ ID NO 14
<211> LENGTH: 23
<212> TYPE: DNA
<213> ORGANISM: Aspergillus oryzae

<400> SEQUENCE: 14
gttacaccaa cgacatagcc ctc                                           23

<210> SEQ ID NO 15
<211> LENGTH: 20
<212> TYPE: DNA
<213> ORGANISM: Aspergillus oryzae

<400> SEQUENCE: 15
caaactggga atgccacaaa                                               20

```
<210> SEQ ID NO 16
<211> LENGTH: 25
<212> TYPE: DNA
<213> ORGANISM: Aspergillus oryzae

<400> SEQUENCE: 16
tgaagacgga gagaactatt ccatg                                           25

<210> SEQ ID NO 17
<211> LENGTH: 23
<212> TYPE: DNA
<213> ORGANISM: Aspergillus oryzae

<400> SEQUENCE: 17
cgctagcaag attagcgatc agt                                             23

<210> SEQ ID NO 18
<211> LENGTH: 22
<212> TYPE: DNA
<213> ORGANISM: Aspergillus oryzae

<400> SEQUENCE: 18
gctttcagct cgatcaacac tg                                              22

<210> SEQ ID NO 19
<211> LENGTH: 22
<212> TYPE: DNA
<213> ORGANISM: Aspergillus oryzae

<400> SEQUENCE: 19
cgtgacaaca tccagggtat ca                                              22

<210> SEQ ID NO 20
<211> LENGTH: 21
<212> TYPE: DNA
<213> ORGANISM: Aspergillus oryzae

<400> SEQUENCE: 20
tcaagcgtat ctctgccatg a                                               21
```

METHOD OF PRODUCING RECOMBINANT PROTEIN

TECHNICAL FIELD

The present invention relates to a method of producing recombinant protein, and more particularly, to a method of producing recombinant protein by using koji molds as host.

BACKGROUND ART

Koji has been utilized as enzyme sources in production of fermented foods and drinks since a long time ago. As koji for producing fermented foods and drinks, there has been conventionally used the solid koji which is obtained by growing koji molds on the surface of cereals and the like. The solid koji is obtained by a traditional production method. However, the method is a special culture mode, that is, solid culture, so unsuitable for large-scale production.

On the other hand, the liquid koji, which is a culture product of koji molds obtained by liquid culturing koji molds, can control culture easily, and a suitable culture mode for efficient production.

However, it is well known that the liquid koji mold does not provide sufficient enzyme activity required for producing fermented foods and drinks, so there are few examples in which the liquid koji is used for actual production (see, Non-patent Documents 1 to 4).

Koji molds easily proliferate, media therefore may be prepared at low cost, and no special culture apparatuses are required, so the cost for culturing is low. The koji molds have been utilized for producing fermented foods and drinks since a long time ago, so are recognized as a safe host. Thus, it has conventionally attempted to incorporate a gene derived from koji molds or from the other organisms by using the koji molds as host to strongly express the genes, to thereby produce products derived from the genes, that is, recombinant proteins (see, Non-patent Document 5).

There also has been reported a successful example of producing recombinant protein in high yields by solid culture with wheat bran (see, Non-patent Document 6). However, the production was performed in a special culture mode, that is, solid culture, so unsuitable for large-scale production.

On the other hand, it has been thought that the liquid culture inherently provides few proteins outside cells as described above, and thus is unsuitable for mass-production of recombinant protein.

Non-patent Document 1: Hata Y. et al.: J. Ferment. Bioeng., 84, 532-537 (1997)

Non-patent Document 2: Hata Y. et al.: Gene, 207, 127-134 (1998)

Non-patent Document 3: Ishida H. et al.: J. Ferment. Bioeng., 86, 301-307 (1998)

Non-patent Document 4: Ishida H. et al.: Curr. Genet., 37, 373-379 (2000)

Non-patent Document 5: R. J. Gouka, et al., Appl. Microbiol. Biotechnol., 47, 1-11 (1997)

Non-patent Document 6: K. Tsuchiya, et al., Biosci. Biotech. Biochem., 58, 895-899 (1994)

DISCLOSURE OF THE INVENTION

Problems to be solved by the Invention

It is an object of the present invention to provide a method of mass-producing recombinant protein by the liquid culture method using koji molds as host, which has been conventionally thought to be unsuitable for producing recombinant protein because of the above-mentioned reasons.

Means for solving the Problems

The inventors of the present invention have already proposed methods of producing liquid koji having sufficient enzyme activities (see, Japanese Patent Application Nos. 2004-350661, 2004-352320, 2004-352324, 2004-378453 and 2005-290648, and JP-A-2003-265165). Those methods use as a medium the raw material of which surface is entirely or partly covered with at least husks to prevent nutrient release from the raw material into the culture system, and thereby required activities of enzymes, in particular, amylolytic enzymes, cellulolytic enzymes and proteolytic enzymes are obtained. According to the methods, it is obtained enzyme activities higher than those obtained by liquid culture using as raw material polished barley or polished rice which is a raw material of shochu. Examples of the koji molds comprise white koji molds, black koji molds, yellow koji molds and red koji molds.

It is assumed that the above-mentioned methods of producing liquid koji increase transcription levels of genes which encode the enzymes affected by the catabolite repression due to concentrations of nutrients such as saccharides and amino acids, and thereby the products (i.e., intended enzymes) derived from those genes are produced and secreted outside cells of the koji molds.

A gene encoding an intended protein is ligated to downstream of the promoter of a gene encoding the enzyme affected by the catabolite repression due to concentrations of nutrients such as saccharides and amino acids, to thereby create recombinant koji molds having incorporated therein the ligated product, culturing the recombinant koji molds according to the above-mentioned methods of producing liquid koji, and therefore, the intended recombinant protein is produced in high yields.

Additional important factor in producing recombinant protein is that the translated recombinant protein is properly transported to outside cells of the host. Even if the transcription levels are simply increased, translated recombinant proteins can often be accumulated in a cell, or decomposed by enzymes inherently secreted by the host. In addition, it is not produced a protein which is properly folded and has activity equivalent to that of a natural protein unless the recombinant protein is subjected to required modification during transportation thereof to outside cells of the host.

It is whereas highly possible to produce and secrete larger number of recombinant proteins by the technique of producing liquid koji as described above with using koji molds as host. An intended recombinant protein may also be obtained in high yields by that it is allowed to be produced outside host koji molds, as a fusion protein of the recombinant protein with the enzyme which is inherently produced and secreted by the host koji molds, and that the fusion protein contained in a culture supernatant is cleaved at the ligation site thereof with site-directed protease.

Based on the above-mentioned findings, the present invention is thus completed.

That is, the present invention according to claim 1 is to provide a method of producing recombinant protein by using the recombinant koji molds which are obtained by transforming koji molds as host comprising: culturing the recombinant koji molds in a liquid medium which contains as culture raw material at least one selected from the group consisting of the cereal of which surface is entirely or partly covered with at least husks, the bean and/or the tuber of which surface is covered with hulls and the amaranthus and/or the quinoa without pre-treatment such as grinding or crushing; and collecting the recombinant protein from the culture product.

The present invention according to claim 2 is to provide the method of producing recombinant protein according to claim 1, in which the recombinant koji molds are obtained by that a gene encoding an intended protein is ligated to downstream of the promoter of a gene encoding the enzyme affected by the catabolite repression due to concentrations of nutrients such as saccharides and amino acids, to thereby obtain a ligated product, and that the ligated product is introduced into koji molds as host.

The present invention according to claim 3 is to provide the method of producing recombinant protein according to claim 2, in which the promoter is a promoter of a gene encoding any one enzyme selected from the group consisting of amylolytic enzymes, cellulolytic enzymes and proteolytic enzymes.

Effects of the Invention

According to the present invention, it is provided a method of mass-producing recombinant protein by liquid culture method with koji molds as host. Koji molds easily proliferate, so media therefore may be prepared at low cost, and no special culture apparatuses are required. The koji molds have been utilized for producing fermented foods and drinks since a long time ago, so are a safe host.

Further, the liquid culture of koji molds can be controlled more strictly as compared to the solid culture, so it is suitable for efficient production.

In addition, a variety of production patterns may be selected by using various raw materials and koji mold strains, and an intended recombinant protein is efficiently and stably mass-produced.

BEST EMBODIMENT FOR CARRYING OUT THE INVENTION

Hereinafter, the present invention will be described in detail.

A liquid medium to be used in the present invention contains at least one culture raw material selected from the group consisting of the cereal of which surface is entirely or partly covered with at least husks, the be an and/or the tuber of which surface is covered with hulls, and the amaranthus and/or the quinoa without pre-treatment such as grinding or crushing.

In the present invention, examples of the cereal to be used as culture raw material comprise barley, rice, wheat, buckwheat, barnyard millet, foxtail millet, millet, kaoliang, corn and the like. The culture raw materials need to have the form of which surface is entirely or partly covered with at least husks. It may be used an unpolished stuff or that having equal to or more of the polyshing ratio at which it has been polished so that husks are at least remained on the surface of kernels, and crude rice, crude barley and the like may also be used. In the case of rice, crude rice, rice with all chaffs and rice with a part of chaffs may be used.

When the culture raw material is barley, the unpolished stuff having a polishing ratio of 100% may be used. Alternatively, provided that the polishing ratio of the unpolished stuff is defined as 100%, the stuff having a polishing ratio not less than the value determined by subtracting the husk ratio of barley (generally 7 to 8%) from the polishing ratio of the unpolished stuff (100%), i.e., about 92% to 93%.

The term "polishing ratio" refers to the remained ratio of cereals after the cereals are polished. For instance, the term "polishing ratio of 90%" means that 10% of the husks or the like on the surface layer portion based on a cereal is shaved away. In the present invention, the term "crude barley" comprises those from unpolished barley to polished barley having husks remained on the kernel surface, that is, the stuff having a polishing ratio of 90% and more. The term "husk" refers to the outside part that covers the surface of a cereal particle.

In the present invention, examples of the bean and the tuber to be used as culture raw material comprise soybean, red bean, sweet potato and the like. Those culture raw materials are only subjected that the soil on their hulls washed away, but are not subjected to processes such as cutting, crushing and the like, and are used for preparing liquid medium with completely covered with the hulls.

In the present invention, beans and tubers as culture raw material may be heat or freeze treated with the hulls thereof remained.

In the present invention, "amaranthus" to be used as culture raw material is a generic term of plants belonging to the genus Amaranthus of the family Amaranthaceae. Among cereals, amaranthus has high protein content and the content of lysine, which is one of amino acids, is equal to that in soybean. Besides, amaranthus is a highly nutritious cereal containing large amounts of calcium, iron, and fibers when compared to polished rice. The countries of origin are specific areas of South/Central American countries, India, Himalayas, and Nepal. On the other hand, quinoa is an annual herb of Agatha family, which is mainly cultivated in highlands such as the Andes located in the southern part of Peru and the western part of Bolivia. Quinoa is rich in minerals, vitamins, proteins, and dietary fibers.

Amaranthus and quinoa to be used as culture raw material may be used alone or in combination. Those raw materials may be directly used for preparing liquid medium without being subjected to pre-treatment such as grinding or crushing.

One of the above-mentioned culture raw materials or a combination of two or more thereof is used for preparing the liquid medium as described below. The above-mentioned culture raw materials are mixed with water to prepare a liquid medium. The blending ratio of the raw material may be adjusted to the extent that an intended recombinant protein is selectively generated and accumulated in the koji mold culture product.

For instance, when barley is used as culture raw material, liquid medium is prepared by adding 1 to 20% (w/vol) of barley to water. When unpolished barley is used, liquid medium is prepared with the addition of more preferably 8 to 10% (w/vol). When 95%-polished barley is used as raw material, liquid medium is prepared with the addition of more preferably 1 to 4% (w/vol).

Next, when unpolished rice from which chaffs are removed is used as culture raw material, liquid medium is prepared by adding 1 to 20%, preferably 5 to 13%, or more preferably 8 to 10% (every value is in w/vol) of unpolished rice to water.

When bean is used as culture raw material, liquid medium is prepared by adding 1 to 10% of bean to water, preferably, by adding 8 to 10% of soybean or 1 to 2% (every value is in w/vol) of red bean to water. When tuber is used as culture raw material, liquid medium is prepared by adding 1 to 10% (w/vol) of tuber to water.

When amaranthus is used as culture raw material, liquid medium is prepared by adding 1.5 to 15%, preferably 2 to 10%, or more preferably 2 to 8% (every value is in w/vol) of amaranthus to water. When quinoa is used as culture raw material, liquid medium is prepared by adding 1.5 to 7%, preferably 2 to 6%, or more preferably 2 to 4% (every value is in w/vol) of quinoa to water.

The amounts of the culture raw materials to be used for the blending may appropriately be selected because the optimal amounts vary dependent on the polishing degrees or the kind of the culture raw materials to be used, the strain of koji molds as host to be used, the promoter to be used, the recombinant protein to be produced and the like.

When the amount of the culture raw material to be used is more than the upper limit, viscosity of the culture liquid increases and supply of oxygen or air required for aerobically culturing recombinant koji molds becomes insufficient. That decrease oxygen content in the culture product, restricts culture progress, and is not preferred. On the other hand, when the amount of the raw material to be used is less than the lower limit, an intended recombinant enzyme is not produced in large amount.

Starches comprised in the culture raw material may be preliminarily gelatinized before culturing. Gelatinizing starches may be performed according, but not particularly limited, to any of the conventional methods comprising a steaming method, a roasting method and the like. Starches may be gelatinized in the step of sterilizing liquid medium as described later when they are heated to the gelation temperature or higher by the sterilization with high temperatures and high pressures.

In addition to the above-mentioned culture raw material, organic substances, inorganic salts, and the like are desirably added as nutrient sources to the liquid medium to be used in the present invention.

For instance, when white koji molds such as *Aspergillus kawachii* or black koji molds such as *Aspergillus awamori* and *Aspergillus niger* are used as host, a nitrate salt and a phosphate salt are preferably used in combination, or more preferably, a sulfate salt is used in combination in addition to them. Examples of the nitrate salt comprise sodium nitrate and potassium nitrate, and potassium nitrate is particularly preferable. Examples of the phosphate salt comprise potassium dihydrogen phosphate and ammonium phosphate, and potassium dihydrogen phosphate is particularly preferable. Examples of the sulfate salt comprise magnesium sulfate heptahydrate, iron sulfate heptahydrate and ammonium sulfate, and magnesium sulfate heptahydrate and iron sulfate heptahydrate are particularly preferable. Two or more of them may be used in combination.

Concentrations of the inorganic salts in liquid medium when the white koji molds or the black koji molds are used are adjusted to the extent that an intended recombinant protein is selectively generated and accumulated in the koji mold culture product. To be specific, the concentration of nitrate salt is 0.1 to 2.0%, preferably 0.2 to 1.5%, the concentration of phosphate salt is 0.05 to 1.0%, preferably 0.1 to 0.5%, and the concentration of sulfate salt is 0.01 to 0.5%, preferably 0.02 to 0.1% (every value is in w/vol).

When yellow koji molds such as *Aspergillus oryzae* and *Aspergillus sojae* are used, a nitrate salt, a phosphate salt and a sulfate salt are preferably used altogether in the liquid medium. Examples of the nitrate salt comprise sodium nitrate and potassium nitrate, and sodium nitrate is particularly preferable. Examples of the phosphate salt comprise potassium dihydrogen phosphate and ammonium phosphate, and potassium dihydrogen phosphate is particularly preferable. Examples of the sulfate salt comprise magnesium sulfate heptahydrate, iron sulfate heptahydrate and ammonium sulfate, and magnesium sulfate heptahydrate and iron sulfate heptahydrate are particularly preferable. Two or more of those inorganic salts may be used in combination.

Concentrations of the inorganic salts in liquid medium when the yellow koji molds are used are adjusted to the extent that an intended recombinant protein is selectively generated and accumulated in the koji mold culture product. To be specific, the concentration of nitrate salt is 0.1 to 2.0%, preferably 0.2 to 1.5%, the concentration of the phosphate salt is 0.05 to 1.0%, preferably 0.1 to 0.5%, and the concentration of sulfate salt is 0.01 to 0.5%, preferably 0.02 to 0.1% (every value is in w/vol).

Organic substances and inorganic salts except the above-mentioned inorganic salts may appropriately be added as nutrient sources to the liquid medium of the present invention. Those additives are not particularly limited as long as they are generally used for culturing koji molds. Examples of the organic substance comprise rice bran, wheat gluten, corn steep liquor, soybean cake, and defatted soybean. Examples of the inorganic salts comprise water-soluble compounds such as an ammonium salt, a potassium salt, a calcium salt, and a magnesium salt. Two or more organic substances and/or inorganic salts may simultaneously be used. The addition amounts thereof are not particularly limited as long as proliferation of the recombinant koji mold is promoted. The addition amount of the organic substance is preferably about 0.1 to 5% (w/vol) and the addition amount of the inorganic salts is preferably about 0.1 to 1% (w/vol).

Addition of those nutrient sources in an amount more than the upper limit is not preferable because growth of the recombinant koji molds is inhibited. An amount less than the lower limit is also not preferable because an intended recombinant protein is not mass-produced.

The liquid medium thus obtained may be subjected to sterilization treatment if necessary and the treatment procedures are not particularly limited. For example, it may be the high-temperature and high-pressure sterilization method carried out at a temperature of 121° C. for 15 minutes.

The sterilized liquid medium is cooled down to a culture temperature, and then the recombinant koji molds are inoculated to the liquid medium.

The recombinant koji molds to be used in the present invention is the stuff obtained by transforming koji molds as host, and may be the stuff cultured with the above-mentioned liquid medium by the culture method as described below. The koji molds to be used as host may be the stuff which produces the enzymes affected by the catabolite repression due to concentrations of nutrients such as saccharides and amino acids. Examples thereof comprise white koji molds such as *Aspergillus kawachii*, black koji molds such as *Aspergillus awamori* and *Aspergillus niger*, and yellow koji molds such as *Aspergillus oryzae* and *Aspergillus sojae*.

The recombinant koji molds of the present invention is obtained by ligating a gene encoding an intended protein to downstream of a promoter, and introducing the ligated product into koji molds as host. Any promoter may be used in the present invention so long as it expresses the downstream gene in the koji molds as host, and it is preferable promoter of the enzyme which is produced in high yields outside cells of the koji molds. It is more preferable to use a promoter of a gene encoding the enzyme affected by the catabolite repression due to concentrations of nutrients such as saccharides and amino acids. Specific examples thereof comprise promoters of the genes encoding amylolytic enzymes such as glucoamylase (GlaA or GlaB) and α-amylase (AmyB), cellulolytic enzymes such as glucanase (EglA) and proteolytic enzymes such as acid protease (PepA).

In the present invention, the recombinant koji molds are cultured by using the above-mentioned culture raw material, so decomposition of nutrients such as saccharides and amino acids in the raw material takes much time, and the releasing rate of nutrients into the culture system is prevented. Accordingly, the promoter of a gene encoding the enzyme affected by the catabolite repression due to concentrations of those nutrients is activated, transcription level of a gene encoding an intended protein which exists downstream of the promoter increases, whereby the intended recombinant protein is mass-produced.

In the present invention, the gene encoding an intended protein may be the stuff which can be expressed in koji molds as host, and may be a cDNA or a chromosomal DNA. In the present invention, the term "protein" comprises glycoproteins. The gene encoding an intended protein is not limited to genes derived from koji molds. Genes derived from other organism species can also be used as long as the genes are suitable for producing recombinant proteins using koji molds as host.

In addition to the promoter and the gene encoding an intended protein, a ligated product having terminator, selection marker and the like ligated therein may optionally be introduced into recombinant koji molds of the present invention. The terminator may be the stuff which functions in the koji molds as host, and it is preferable to use a terminator of the enzyme which is produced in high yields outside cells of the koji molds.

In the present invention, transformation of the koji molds as host may be performed by a typical method such as the method of introducing a plasmid vector into a protoplast of the host under the presence of PEG (Unkles, et al., Mol. Gen. Genet., 218, 99-104 (1989)).

Any plasmid may be used for the vector so long as it is suitable for the host koji molds. For instance, the plasmid may be created by using pPTRIDNA, pPTRIIDNA (TAKARA BIO INC.) and the like dependent on the purposes. However, the plasmid is not limited to those.

In order to introduce a gene encoding the above-mentioned intended protein into the above-mentioned vector, a well-known method may be employed. One of the method comprises, cleaving a purified gene encoding the intended protein with an appropriate restriction enzyme, inserting the cleaved gene into the restriction enzyme site or the multicloning site of an appropriate vector DNA, to thereby ligate the cleaved gene to the vector.

The koji molds transformed as described above are cultured using an appropriate selection medium. After that, a resultant colony is isolated to obtain the recombinant koji molds in which a gene encoding an intended protein is incorporated.

Thus-obtained recombinant koji molds may be used for the single strain culture, or for the mixed culture with two or more homologous or heterogeneous strains. It is allowed to use either form of the spores or the mycelia obtained in pre-culture. However, the mycelia are preferably used because shorter period of time is required for the logarithmic growth phase. The amount of the recombinant koji molds to be inoculated to the liquid medium is not particularly limited, but the number of the spores may be in the range of about $1\times10^4$ to $1\times10^6$ per ml of the liquid medium. For the mycelia, about 0.1 to 10% of the pre-culture liquid is preferably inoculated.

The culture temperature of the recombinant koji molds may preferably be set to 25 to 45° C., or more preferably 30 to 40° C., but is not particularly limited as long as the growth is not adversary affected. If the culture temperature is low, it tends to be contaminated with infectious microbes as growth of the recombinant koji molds becomes slow.

When yellow koji molds are used as host, the enzyme activity is enhanced by controlling the culture temperature in accordance with growing phase of the yellow koji molds. To be specific, the culture temperature may be maintained at 25 to 35° C., preferably 28 to 33° C. during proliferative phase of cells, which starts at initiation of the culture and terminates after 12 to 36 hours from the initiation, and during subsequent enzyme production phase, 35 to 45° C., preferably 37 to 42° C.

The culture apparatus may be any of those capable of carrying out liquid culture. The koji molds have to be cultured aerobically, so the culture should be performed under aerobic conditions in which oxygen or air is supplied into the medium. In addition, it is preferable to stir the medium during the culture so that the raw material, oxygen, and the recombinant koji molds are uniformly distributed in the apparatus during culture. The stirring conditions and the amount of aeration may be arbitrary as long as the culture environment be maintained aerobically, and may appropriately be selected dependent on the culture apparatus, the viscosity of the medium and the like.

The recombinant koji molds are cultured by the above-mentioned culture method to produce an intended recombinant protein in high yields in the culture product.

In the present invention, the recombinant protein is then collected from the resultant koji mold culture product. Any well-known technique may be used for the method of collecting the recombinant protein. For instance, it is adopted the method of that the culture product is filtrated, centrifuged or the like to obtain a culture supernatant, and that the culture supernatant is optionally concentrated, purified or the like by using an adsorption resin, electrophoresis or the like.

EXAMPLES

Hereinafter, the present invention will be described in more detail by way of examples and the like. However, the present invention is not limited thereto.

Example 1

Method of Producing Recombinant Protein by Using Yellow Koji Molds as Host (Preparation of Medium)

Composition of the liquid medium for yellow koji molds was as follows: 2.0% of 98%-polished barley (Starling, made in Australia), 1.2% of sodium nitrate, 0.8% of potassium chloride, 0.4% of potassium dihydrogen phosphate, 0.2% of magnesium sulfate heptahydrate and 0.08% of iron sulfate heptahydrate (every value is in w/vol).

For the control, the DPY medium (containing 2% of dextrin, 1% of polypeptone, 0.5% of yeast extract, 0.5% of potassium dihydrogen phosphate and 0.05% of magnesium sulfate (every value is in w/vol)) was used.

20 ml each of the media was put in a 100-ml baffled conical flask, respectively, and sterilized with autoclave at 121° C. for 15 minutes.

(Recombinant Koji Mold)

It was used as recombinant koji molds the niaD 300-Der fI which has been deposited with Accession No. FERM BP-10667 in International Patent Organism Depositary, National Institute of Advanced Industrial Science and Technology, Tsukuba Central 6, 1-1-1 Higashi, Tsukuba, Ibaraki, Japan (Old name and address: Fermentation Research Institute, Agency of Industrial Science and Technology, Ministry of International Trade and Industry, 1-1-3 Higashi, Tsukuba, Ibaraki, Japan) on Jul. 30, 1997 and which has been transferred to the international depository from the original depository on Aug. 28, 2006. The recombinant koji mold niaD 300-Der fI was obtained according to a method described in JP-A-11-75840, using as host a nitrate-assimilation mutant strain niaD 300 of *Aspergillus oryzae* by incorporating thereto Der fI E(-1)K, that is, a DNA fragment obtained by altering a glutamic acid codon at the 3' terminal into a lysine codon in pro-sequence of cDNA of the glycoprotein Der fI, which is a main allergen present in *Dermatophagoides farinae* (see, H. Shoji, et al., Biosci. Biotechnol. Biochem., 61(10), 1668-1673, 1997).

In the niaD 300-Der fI DNA, a glaA promoter derived from *Aspergillus oryzae* is ligated upstream of the Der fI E(-1)K DNA and an amyB terminator derived from *Aspergillus oryzae* is ligated downstream of the Der fI E(-1)K DNA.

(Culture of Recombinant Koji Molds)

About $10^6$ conidia of the obtained recombinant koji mold niaD 300-Der fI were inoculated to 20 ml each of the media obtained as described above, respectively, and cultured with shaking at 30° C. and 100 rpm for 24 hours.

(Purification of Recombinant Protein Der fI E(-1)K)

After the liquid culture was completed, each of the culture liquids was centrifuged at 3,000×g and 4° C. for 10 minutes. Endoglycosidase Hf (Biolabs Company) was directly added in a concentration of 10 units/ml to the culture supernatant and was allowed to react while maintaining at 37° C. for 3 hours, to thereby performing trimming of saccharide chains. The resultant reaction liquid was passed through a strong anion exchange column (Trade name: QMA, Waters Corporation) which had been equilibrated with 20 mM phosphate buffer solution (pH 6.0) to adsorb α-amylase, a large amount of which present in the reaction liquid. Lysyl endopeptidase (Wako Pure Chemical Industries Inc.) was added to the fraction which had passed without being adsorbed on the QMA column so that the final concentration is 10 μg/ml to cleave the Der fI E(-1)K pro-sequence. After that, the resultant was dialyzed against 50 mM Tris-HCl (pH 9.0) overnight at 4° C.

The concentrate thus obtained was directly charged onto a DEAE-Sephacel column (Amersham Bio-Sciences K.K.) which had been equilibrated with 50 mM Tris-HCl (pH 8.0), and then washed with 20 mM Tris-HCl (pH 8.0) in an amount of 3 times that of the column. Subsequently, the mature recombinant protein Der fI E (-1)K which had been adsorbed to the column was eluted by using NaCl concentration gradient. A fraction containing the mature recombinant protein Der fI E(-1) K was detected by Western analysis using anti-Der fI antibody to collect fractions having high purity, and were used as a purified sample. Purity of the purified sample was confirmed to be 90% or more by sodium dodecyl sulfate-polyacrylamide gel electrophoresis (SDS-PAGE).

The purified sample was subjected to a quantitative analysis of protein by using BCA Protein Assay Reagent Kit (Pierce Biotechnology, Inc.).

(Results) Yield of Recombinant Protein Der fI E(-1)K

When the DPY medium was used, about 8 mg of the mature recombinant protein Der fI E(-1)K per L of the medium was obtained. When the liquid medium for yellow koji molds was used, about 24 mg of the mature recombinant protein Der fI E(-1)K per L of the medium was obtained.

In this manner, it is found that, according to the present invention, a recombinant protein was produced in an amount of three times as much as that produced by the method of using the conventional DPY medium.

The recombinant protein Der fI E (-1) K had a saccharide chain different from that of the natural Der fI. However, the recombinant protein Der fI E(-1)K exhibited the IgE-binding ability and the skin irritancy which were equivalent to those of the natural Der fI. Thus, the recombinant protein is utilized as an alternative to the natural Der fI for preparing antibody, treatment of allergy and the like.

Experimental Example 1

Measurement of Promoter Activities of Various Enzyme Genes in White Koji Molds for Shochu In order to confirm that promoters of various enzyme genes in white koji molds are usable for the present invention, expression levels of those promoters were measured by the following method.

<Strain to be Used> *Aspergillus kawachii* NBRC4308

<Culture conditions> Composition of the medium was as follows: 2.0% of 98%-polished barley (Starling, made in Australia), 0.2% of sodium nitrate and 0.3% of potassium dihydrogen phosphate (every value is in w/vol). 100 ml of the medium was put in a 500-ml baffled conical flask, and sterilized with autoclave at 121° C. for 15 minutes. About $10^6$ conidia of *Aspergillus kawachii* NBRC4308 were inoculated to 100 ml of the medium obtained as described above, and cultured with shaking at 37° C. and 100 rpm for 18 hours.

For the comparative control, culture was performed with the same medium composition and culture conditions as described above except that 65%-polished barley or 98%-polished barley crushed product (both of them were Stirling, made in Australia) was employed in the medium instead of the 98%-polished barley.

<Preparation of Total RNA> After the culture was completed, the cells were rapidly collected and crushed well under the presence of liquid nitrogen. From the crushed koji mold cells, total RNA was prepared by using a total RNA extraction kit (i.e., RNeasy Plant mini kit, manufactured by QIAGEN) according to its protocol.

<Preparation of cDNA> From the resultant total RNA, cDNA was synthesized by using a High-capacity cDNA Archive Kit (manufactured by Applied Biosystems) according to its protocol.

<Quantitative real time PCR> Quantitative real time PCR was performed by using the resultant cDNA as template and by using the primers designed on the basis of base sequences of intended enzyme genes as described below, to thereby quantify expression levels of the enzyme genes. The primers used in the quantitative real time PCR were each designed by using Primer Express software (manufactured by Applied Biosystems). The primer sequences are represented specifically as described below. H2A gene encoding histone was used as the internal standard for the comparative quantification method.

PCR and signal detection were performed by using SYBR Green PCR Master Mix (manufactured by Applied Biosystems) as reagent for the quantitative real time PCR, according to an appended protocol. The PCR and the signal detection were performed by using ABI PRISM 7700 (manufactured by Applied Biosystems).

<Genes and Primer Sequences which were Used>

(1) Glucoamylase gla-1 (derived from *Aspergillus kawachii*, GenBank Accession No. D00427)

```
                         (SEQ ID NO: 1 in Sequence Listing)
    Forward primer: 1589-ccagctcgacctatagcagcat (SEQ ID NO: 2)
    Reverse primer: 1761-aagtctgatggcgacgagct
```

The pair of the primers was designed so as to amplify the DNA fragment composed of the 1,589th to 1,780th bases of the above-mentioned gla-1 (GenBank Accession No. D00427).

(2) Acid-stable α-amylase asaA (derived from *Aspergillus kawachii*, GenBank Accession No. AB008370)

```
                                         (SEQ ID NO: 3)
Forward primer:  994-cggcacggcagatgatc (SEQ ID NO: 4)
Reverse primer:  1044-gaatgtacctcatggtcgacgtc
```

The pair of the primers was designed so as to amplify the DNA fragment composed of the 994th to 1,066th bases of the above-mentioned asaA (GenBank Accession No. AB008370).

(3) α-amylase amyA (derived from *Aspergillus kawachii*, GenBank Accession No. AB109452)

```
                                         (SEQ ID NO: 5)
Forward primer:  1874-acactcctgggcacattcg (SEQ ID NO: 6)
Reverse primer:  1989-ttacaccaacgacatagccct
```

The pair of the primers was designed so as to amplify the DNA fragment composed of the 1,874th to 2,009th bases of the above-mentioned amyA (GenBank Accession No. AB109452).

(4) Histone H2A (derived from *Aspergillus niger*, GenBank Accession No. Y15320)

```
                                         (SEQ ID NO: 7)
Forward primer:  289-actgaacaagctcctgggtca (SEQ ID NO: 8)
Reverse primer:  322-ccagggtggtgtcctcccc
```

The pair of the primers was designed so as to amplify the DNA fragment composed of the 289th to 340th bases of the above-mentioned H2A (GenBank Accession No. Y15320).

<Results> Expression levels of the respective enzyme genes were quantitated as values relative to an expression level of the histone H2A. Table 1 shows the results. In the experimental plots (the present invention) in which 98%-polished barley was used, the expression levels of the respective genes increased as compared to those in the control plots. Thus, it was revealed that the promoters of those enzyme genes were effectively used in the method of producing recombinant protein of the present invention.

TABLE 1

| | Used raw material | Expression level |
|---|---|---|
| gla-1 | The present invention (98%-polished barley) | 8.49 |
| | Control 1 (98%-polished barley crushed product) | 3.95 |
| | Control 2 (65%-polished barley) | 2.35 |
| asaA | The present invention (98%-polished barley) | 2.89 |
| | Control 1 (98%-polished barley crushed product) | 1.99 |
| | Control 2 (65%-polished barley) | 1.05 |
| amyA | The present invention (98%-polished barley) | 23.86 |
| | Control 1 (98%-polished barley crushed product) | 17.65 |
| | Control 2 (65%-polished barley) | 14.59 |

Experimental Example 2

Measurement of Promoter Activities of Enzyme Genes in Black Koji Molds for Shochu In order to confirm that promoters of various enzyme genes in black koji molds are usable for the present invention, expression levels of those promoters were measured by the following method.

That is, *Aspergillus awamori* NBRC4388 was cultured by the method same as that in Experimental Example 1. After that, total RNA was extracted from the cells obtained after completion of the culture in the same manner as in Experimental Example 1, and cDNA was synthesized. Further, expression levels of the intended enzyme genes as described below were quantitated by using the resultant cDNA as template in the same manner as in Experimental Example 1. The primer sequences used in quantitative real time PCR were as described below.

<Genes and Primer Sequences which were Used>

(1) α-amylase amyA (The Same amyA as Described in Experimental Example 1)

The same pair of the primers (SEQ ID NOS: 5 and 6) as in Experimental Example 1 was used.

(2) Acid protease pepA (Derived from *Aspergillus awamori*, GenBank Accession No. M34454)

```
                              (SEQ ID NO: 9 in Sequence Listing)
Forward primer:  793-ttttgggactggcctttagct (SEQ ID NO: 10)
Reverse primer:  900-ttcttcgacaccgtcaagtcc
```

The pair of the primers was designed so as to amplify the DNA fragment composed of the 793rd to 920th bases of the above-mentioned pepA (GenBank Accession No. M34454).

(3) Histone H2A (The Same H2A as Described in Experimental Example 1)

The same pair of the primers (SEQ ID NOS: 7 and 8) as in Experimental Example 1 was used.

<Results> Expression levels of the respective enzyme genes were quantitated as values relative to an expression level of the histone H2A. Table 2 shows the results. In the experimental plots (the present invention) in which 98%-polished barley was used, the expression levels of the respective genes increased as compared to those in the control plots. Thus, it was revealed that the promoters of those enzyme genes were effectively used in the method of producing recombinant protein of the present invention.

TABLE 2

| | Used raw material | Expression level |
|---|---|---|
| amyA | The present invention (98%-polished barley) | 19.1 |
| | Control 1 (98%-polished barley crushed product) | 0.1 |
| | Control 2 (65%-polished barley) | 0.3 |
| pepA | The present invention (98%-polished barley) | 2.4 |
| | Control 1 (98%-polished barley crushed product) | 0.7 |
| | Control 2 (65%-polished barley) | 1.5 |

Experimental Example 3

Measurement of Promoter Activities of Enzyme Genes in Yellow Koji Molds for Sake In order to confirm that promoters of various enzyme genes in yellow koji molds are usable in the present invention, expression levels of those promoters were measured by the following method.

<Strain to be Used> Aspergillus oryzae NRIB40

<Culture conditions> Composition of the medium was as follows: 2.0% of 98%-polished barley (Starling, made in Australia), 1.2% of sodium nitrate, 0.8% of potassium chloride, 0.4% of potassium dihydrogen phosphate, 0.2% of magnesium sulfate heptahydrate and 0.08% of iron sulfate heptahydrate (every value is in w/vol). 100 ml of the medium was put in a 500-ml baffled conical flask, and sterilized with autoclave at 121° C. for 15 minutes. About $10^6$ conidia of Aspergillus oryzae RIB40 were inoculated to 100 ml of the medium obtained as described above, and cultured with shaking at 30° C. and 100 rpm for 42 hours.

For the comparative control, culture was performed with the same medium composition and culture conditions as described above except that 65%-polished barley or 98%-polished barley crushed product (both of them were Stirling, made in Australia) was used instead of the 98%-polished barley.

After that, total RNA was extracted from the cells obtained after completion of the culture in the same manner as in Experimental Example 1, and cDNA was synthesized. Further, expression levels of the intended enzyme genes as described below were quantitated by using the resultant cDNA as template in the same manner as in Experimental Example 1. The sequences of the primers used in quantitative real time PCR were as described below. H4 gene encoding histone was used as the internal standard for the comparative quantification method.

<Genes and Primer Sequences which were Used>

(1) Glucoamylase glaA (derived from Aspergillus oryzae, GenBank Accession No. D01035)

```
                        (SEQ ID NO: 11 in Sequence Listing)
    Forward primer: 1247-cgtgcagatcgtccaaacct (SEQ ID NO: 12)
    Reverse primer: 1357-acttctcacggccaacaacc
```

The pair of the primers was designed so as to amplify the DNA fragment composed of the 1,247th to 1,376th bases of the above-mentioned glaA (GenBank Accession No. D01035).

(2) α-amylase amyA (derived from Aspergillus oryzae, GenBank Accession No. AB021876)

```
                        (SEQ ID NO: 13)
    Forward primer: 21762-cactcctgggcacattcgt (SEQ ID NO: 14)
    Reverse primer: 21875-gttacaccaacgacatagccctc
```

The pair of the primers was designed so as to amplify the DNA fragment composed of the 21,762nd to 21,897th bases of the above-mentioned amyA (GenBank Accession No. AB021876).

(3) β-glucanase celB (derived from Aspergillus oryzae, GenBank Accession No. D83732)

```
                        (SEQ ID NO: 15)
    Forward primer: 1137-caaactgggaatgccacaaa (SEQ ID NO: 16)
    Reverse primer: 1187-tgaagacggagagaactattccatg
```

The pair of the primers was designed so as to amplify the DNA fragment composed of the 1,137th to 1,211th bases of the above-mentioned celB (GenBank Accession No. D83732).

(4) Acid protease pepA (derived from Aspergillus oryzae, GenBank Accession No. D13894)

```
                        (SEQ ID NO: 17)
    Forward primer: 897-cgctagcaagattagcgatcagt (SEQ ID NO: 18)
    Reverse primer: 958-gctttcagctcgatcaacactg
```

The pair of the primers was designed so as to amplify the DNA fragment composed of the 897th to 979th bases of the above-mentioned pepA (GenBank Accession No. D13894).

(5) Histone H4 (derived from Aspergillus oryzae, GenBank Accession No. AB033943)

```
                        (SEQ ID NO: 19)
    Forward primer: 110-cgtgacaacatccagggtatca (SEQ ID NO: 20)
    Reverse primer: 171-tcaagcgtatctctgccatga
```

The pair of the primers was designed so as to amplify the DNA fragment composed of the 110th to 191st bases of the above-mentioned H4 (GenBank Accession No. AB033943).

<Results> Expression levels of the respective enzyme genes were quantitated as values relative to an expression level of the histone H4. Table 3 shows the results. In the experimental plots (the present invention) in which 98%-polished barley was used, the expression levels of the respective genes increased as compared to those in the control plots. Thus, it was revealed that the promoters of those enzyme genes were effectively used in the method of producing recombinant protein of the present invention.

TABLE 3

| | Used raw material | Expression level |
|---|---|---|
| glaA | The present invention (98%-polished barley) | 0.31 |
| | Control 1 (98%-polished barley crushed product) | 0.04 |
| | Control 2 (65%-polished barley) | 0.10 |
| amyA | The present invention (98%-polished barley) | 21.0 |
| | Control 1 (98%-polished barley crushed product) | 3.3 |
| | Control 2 (65%-polished barley) | 9.3 |
| celB | The present invention (98%-polished barley) | 0.018 |
| | Control 1 (98%-polished barley crushed product) | 0.003 |
| | Control 2 (65%-polished barley) | 0.006 |
| pepA | The present invention (98%-polished barley) | 0.15 |
| | Control 1 (98%-polished barley crushed product) | 0.07 |
| | Control 2 (65%-polished barley) | 0.05 |

INDUSTRIAL APPLICABILITY

According to the present invention, it is provided a method of mass-producing recombinant protein by using koji molds as host. Koji molds are cultured in inexpensive media, and do not require special culture apparatuses, so a desired protein is produced at low cost. In addition, the koji molds have been utilized for producing fermented foods and drinks since a long time ago, and are highly safe as host, and the resulting recombinant proteins may be used for various purposes.

The invention claimed is:

1. A method of producing recombinant protein by using recombinant koji molds which are obtained by introducing a gene product obtained by ligating a gene encoding an intended protein to downstream of a native promoter of a gene encoding any enzyme selected from the group consisting of glucoamylase from *Aspergillus kawachii*, *Aspergillus awamori*, *Aspergillus niger* or *Aspergillus oryzae*, acid stable or-amylase from *Aspergillus kawachii* or *Aspergillus niger*, α-amylase from *Aspergillus kawachii*, *Aspergillus awamori*, *Aspergillus niger* or *Aspergillus oryzae* and acid protease from *Aspergillus awamori*, *Aspergillus niger* or *Aspergillus oryzae*, into white koji molds or black koji molds as host; or using recombinant koji molds which are obtained by introducing a gene product obtained by ligating a gene encoding an intended protein to downstream of a native promoter of a gene encoding any enzyme selected from the group consisting of glucoamylase from *Aspergillus kawachii*, *Aspergillus awamori*, *Aspergillus niger* or *Aspergillus oryzae*, α-amylase from *Aspergillus kawachii*, *Aspergillus awamori*, *Aspergillus niger* or *Aspergillus oryzae*, β-glucanase from *Aspergillus kawachii*, *Aspergillus niger* or *Aspergillus oryzae* and acid protease from *Aspergillus awamori*, *Aspergillus niger* or *Aspergillus oryzae*, into yellow koji molds as host: wherein the native promoter has a catabolite repression, comprising:
   culturing the recombinant koji molds, said recombinant koji molds not being in a solid koji, in a liquid medium which comprises barley and/or wheat having the surface of which entirely or partially covered with husks, wherein crushed products are excluded, thereby decreases the catabolite repression to expresses the intended protein; and
   collecting the recombinant protein from the culture product.

2. The method of producing recombinant protein according to claim 1, wherein the barley and/or wheat the surface of which is entirely or partially covered with husks is polished barley and/or wheat having a polishing ratio of more than 93%.

3. The method of producing recombinant protein according to claim 1, wherein the culture raw material is composed of barley having the surface entirely covered with husks.

4. The method of producing recombinant protein according to claim 1, wherein the barley and/or wheat has the surface of which partially covered with husks.

5. The method of producing recombinant protein according to claim 1, wherein the white koji molds as host are *Aspergillus kawachii*, the black koji molds as host are *Aspergillus awamori* or *Aspergillus niger*, and the yellow koji molds as host are *Aspergillus oryzae* or *Aspergillus sojae*.

6. The method of producing recombinant protein according to claim 1, wherein the native promoter of a gene encoding any enzyme selected from the group consisting of glucoamylase, acid stable α-amylase, α-amylase and acid protease from a koji mold is from a koji mold selected from the groups consisting of *Aspergillus kawachii, Aspergillus awamori*, and *Aspergillus niger*.

7. The method of producing recombinant protein according to claim 1, wherein the native promoter of a gene encoding any enzyme selected from the group consisting of glucoamylase, α-amylase, β-glucanase and acid protease from a koji mold is from a koji mold selected from the group consisting of *Aspergillus oryzae* and *Aspergillus sojae*.

8. The method of producing recombinant protein according to claim 1, wherein the native promoter is of a gene selected from the group consisting of glucoamylase gene (gla-1) as set forth in GenBank Accession No. D00427, the acid-stable α-amylase gene (amyA) as set forth in GenBank Accession No. AB008370, the α-amylase gene (amyA) as set forth in GenBank Accession No. AB109452, the acid protease gene (pepA) as set forth in GenBank Accession No. M34454, the glaA gene as set forth in GenBank Acc. No. D01035, the amyA gene as set forth in GenBank Acc. No. AB021876, the p-glucanase gene (celB) as set forth in GenBank Acc. No. D83732 and the pepA gene as set forth in GenBank Acc. no. D13894.

* * * * *